United States Patent [19]
Bloodsaw

[11] Patent Number: 5,409,016
[45] Date of Patent: Apr. 25, 1995

[54] ORAL CONDOM FOR PREVENTING SEXUALLY TRANSMITTED DISEASES

[76] Inventor: Paula A. Bloodsaw, 67 Manchester, Apt. D, San Francisco, Calif. 94110

[21] Appl. No.: 198,283

[22] Filed: Feb. 18, 1994

Related U.S. Application Data

[62] Division of Ser. No. 154,133, Nov. 18, 1993, Pat. No. 5,320,112.

[51] Int. Cl.6 ............................ A61F 6/02; A61F 6/04
[52] U.S. Cl. .................................... 128/842; 128/844; 128/918
[58] Field of Search ....................... 128/842, 844, 918; 604/347-353; 2/2

[56] References Cited

U.S. PATENT DOCUMENTS

| | | |
|---|---|---|
| 1,986,988 | 1/1935 | Treadwell . |
| 2,123,343 | 7/1938 | Rightsell . |
| 4,781,709 | 11/1988 | Grubman .............................. 128/844 |
| 4,815,456 | 3/1989 | Rubin et al. . |
| 4,855,169 | 8/1989 | McGlothlin ......................... 128/842 |
| 4,949,731 | 8/1990 | Harding ............................... 128/842 |
| 4,955,708 | 9/1990 | Kahaney . |
| 4,967,767 | 11/1990 | Harris et al. . |
| 5,016,649 | 5/1991 | Johnson . |

FOREIGN PATENT DOCUMENTS 9013277  11/1990  WIPO .................................. 128/918

*Primary Examiner*—Michael A. Brown
*Attorney, Agent, or Firm*—Thomas I. Rozsa; Tony D. Chen

[57] ABSTRACT

The present invention is an oral condom which protects the user from contracting sexually transmitted diseases while engaging in oral, vaginal or anal sex. The oral condom provides an improved protective mask which is capable of protecting the facial area of a user from undesirable exposure to infection carrying microorganisms. The oral condom is shaped like an oval with two lateral leg portions which are attached to two ear attachments respectively. The oral condom includes conformed portions for the lips so that the lips can be more easily moved in a natural way and an extended portion for the tongue so the tongue can move in a natural way and not be hindered by the oral condom.

9 Claims, 1 Drawing Sheet

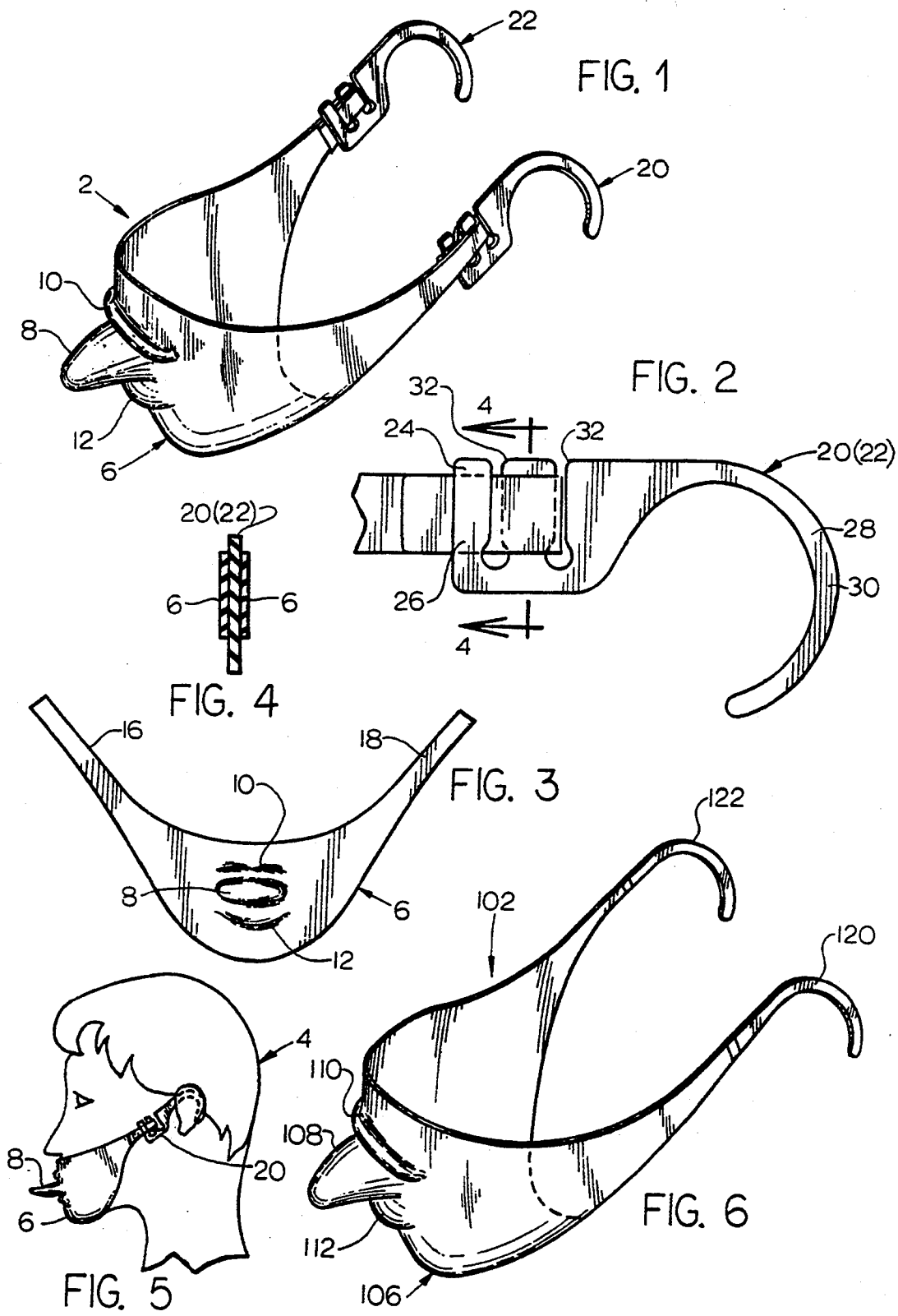

ORAL CONDOM FOR PREVENTING SEXUALLY TRANSMITTED DISEASES

This patent application is a divisional patent application of application Ser. No. 08/154,133 filed on Nov. 18, 1993, now U.S. Pat. No. 5,320,112.

BACKGROUND OF THE INVENTION

1. Field of The Invention

The present invention relates to the field of condoms. In particular, the present invention relates to the field of protective masks utilized in oral, vaginal and anal sex.

2. Description of The Prior Art

The practice of oral sex has been prevalent in our society throughout the ages. Traditionally, however, most couples performing oral sex do not wear any kind of protective mask on their faces so that the face, tongue and lips are protected against sexually transmitted diseases (STD's) and the well-known Acquired Immune Deficiency Syndrome (AIDS). It is known that people who have unsafe sex are the ones that transmit communicable sexually transmitted diseases. STD's and AIDS are widespread throughout the United States and all over the world, and are a major concern to many who engage in sexual activities including oral sex. AIDS and other sexually transmitted diseases will continue to spread throughout the world until there are safe devices for protecting a couple or a prostitute while engaging in sexual activities including oral sex.

There are several different types of protective masks disclosed in the prior art. However these devices have many disadvantages. One disadvantage of prior art devices is that they only minimally cover the lips of the user and consequently leave substantial areas of the face of the user exposed, thereby leaving the user at risk. Another disadvantage of prior art protective masks is that they are affixed in place by strings on the head of a user. Securing these devices to the face of a user is a very time consuming process and users often complain that this process is overly burdensome and cuts down on the "spontaneity" of the sexual act that they wish to enjoy. Another disadvantage of prior art protective masks is that in order to remove the device after the sexual act is concluded, the user has to untie the strings which can prove to be a problem if the knot is tied too tightly. A further disadvantage of prior art devices is that they limit the freedom of movement of the jaw, tongue and lips of a user which further limits the user's desired activities.

The following six (6) prior art patents were uncovered in the pertinent field of the present invention.

1. U.S. Pat. No. 1,986,988 issued to Treadwell on Jan. 8, 1935 for "Application For Mouth Suction" (hereafter "the Treadwell Patent").
2. U.S. Pat. No. 2,123,343 issued to Rightsell on Jul. 12, 1938 for "Sanitary Cover For A Body Organ" (hereafter "the Rightsell Patent").
3. U.S. Pat. No. 4,955,708 issued to Kahaney on Sep. 11, 1990 for "Sunglasses Having Adjustable Temples" (hereafter "the Kahaney Patent").
4. U.S. Pat. No. 4,815,456 issued to Rubin et al. on Mar. 28, 1989 for "Hygienic Device" (hereafter "the Rubin Patent").
5. U.S. Pat. No. 4,967,767 issued to Harris et al. on Nov. 6, 1990 for "Vaginal Shield For Preventing Sexually Transmitted Diseases" (hereafter "the Harris Patent").
6. U.S. Pat. No. 5,016,649 issued to Johnson on May 21, 1991 for "Protective Mask" (hereafter "the Johnson Patent").

The Treadwell Patent discloses an applicator for a mouth suction. The device includes a rectangular shield with a nipple or bag-like portion which is pressed against the part of the shield surrounding an opening. The shield covers the mouth and lips of the user with the nipple extending into the mouth so that by placing the open end of the nipple against a wound, such as a snake bite, pressure and suction can be exerted on the wound and thus the poison in the wound can be drawn into the nipple.

The Rightsell Patent discloses a sanitary cover for a body organ. It includes a tubular portion which is integrated with a shield.

The Kahaney Patent discloses sunglasses having adjustable temples. The sunglasses have temple assemblies which are formed from elongated members which have a sleeve portion formed at their rear end. A leg member is telescopically received in the sleeve portion.

The Rubin Patent discloses a hygienic device. The device includes a thin planar pliable membrane with two end portions. The end portions has straps for stretching over and positioning around the ears.

The Harris Patent discloses a vaginal shield for preventing sexually transmitted diseases. It includes a shield support strap structure that fits over the lower portion of a female user's body. A shield member completely covers the vagina, and it extends downwardly under the crotch of the person wearing the shield. The Harris device is cumbersome and probably is not effective in protecting the user from potential exposure to sexually transmitted diseases during cunnilingus.

The Johnson Patent discloses a protective mask. The mask is formed by an elongated planar membrane of a virus impermeable tough film material. The mask defines a lateral extension portion for extending downwardly and rearwardly over the chin of a wearer. The membrane also has a flaccid pouch-like central portion for accommodating free movement of the tongue of a wearer. The mask is secured to the head of the wearer by strings which are secured to end portions of the membrane and to the lateral extension portion. The mask provides a greater tension which results in less mobility and movement.

Therefore, there is always a need for improved protective masks for the consumer market, so that a user engaging in oral, vaginal and anal sex will be protected from communicable diseases. It is desirable to design an oral condom which prevents exposure to sexually transmitted diseases when engaging in oral, vaginal and anal sex. It is also desirable to design an oral condom which is easy and safe to use by a user, so that the user can enjoy the pleasures of oral sex without fear of contracting AIDS or other diseases.

SUMMARY OF THE INVENTION

The present invention is an oral condom which protects the user from contracting sexually transmitted diseases while engaging in cunnilingus and anal sex. The oral condom provides an improved protective mask which is capable of protecting the facial area of a user from undesirable exposure to infection carrying microorganisms.

It has been discovered, according to the present invention, that by utilizing detachable ear attachments for an oral condom, it will provide a removable and reusable ear attachment and the oral condom can be adjusted to any particular user.

It has further been discovered, according to the present invention, that by utilizing the oral condom which conforms to the lips and tongue of a user, it will provide the tongue with more flexibility.

It is therefore an object of the present invention to provide an oral condom, so that the oral condom can provide protection to a user from sexually transmitted diseases while engaging in oral, vaginal and anal sex.

It is also an object of the present invention to provide an oral condom which has removable ear attachments, so that the tension on the oral condom against the face of a user can easily be adjusted, and the ear attachments can be reused with another oral condom.

It is an additional object of the present invention to provide an oral condom which has a protuberance for accommodating the tongue of a user, so that the tongue can move more readily.

It is also an object of the present invention to provide an efficient and easy to use oral condom which is disposable after use, and used for spontaneous use, with the ear attachments easily and removably affixed to the oral condom such that the ear attachments can be reused with another oral condom.

It is a further object of the present invention to provide an efficient and easy to use oral condom which is a unitary member and is totally disposable after use.

In the preferred embodiment of the present invention, the oral condom comprises a thin pliable oval-shaped membrane with two detachable ear attachments.

In an alternative embodiment of the present invention, the oral condom is a unitary thin pliable unitary membrane with two permanently affixed ear attachments.

Further novel features and other objects of the present invention will become apparent from the following detailed description, discussion and the appended claims, taken in conjunction with the drawings.

BRIEF DESCRIPTION OF THE DRAWINGS

Referring particularly to the drawings for the purpose of illustration only and not limitation, there is illustrated:

FIG. 1 is a perspective view of the preferred embodiment of the present invention oral condom.

FIG. 2 is an enlarged side elevational view of a detachable ear attachment.

FIG. 3 is a front elevational view of the oral condom.

FIG. 4 is a cross-sectional view of the detachable ear attachment taken along line 4—4 of FIG. 2.

FIG. 5 is a side elevational view of the oral condom utilized with a user.

FIG. 6 is a perspective view of an alternative embodiment of the present invention oral condom which is a unitary piece.

DESCRIPTION OF THE PREFERRED EMBODIMENT

Although specific embodiments of the present invention will now be described with reference to the drawings, it should be understood that such embodiments are by way of example only and merely illustrative of but a small number of the many possible specific embodiments which can represent applications of the principles of the present invention. Various changes and modifications obvious to one skilled in the art to which the present invention pertains are deemed to be within the spirit, scope and contemplation of the present invention as further defined in the appended claims.

Referring to FIGS. 1, 3 and 5, there is shown at 2 an oral condom or a protective mask used in conjunction with a user 4 for preventing sexually transmitted diseases when engaging in oral, vaginal or anal sex. The oral condom 2 is generally a thin pliable oval-shaped membrane 6 which is disposable after use. The thin flexible oval-shaped membrane 6 protects all areas of the face used in oral sex and extends from approximately beneath the nostrils to below the chin and jaw, and substantially all of the cheeks, as shown in FIG. 5.

The thin membrane 6 has a conformed shape which has upper and lower lips 10 and 12 for engaging with the lips of a user. The upper lip 10 and the lower lip 12 of the thin membrane 6 are loose so that they will contour and expand with movement for a freer movement so that the user will experience a more natural close feeling when performing oral, vaginal or anal sex. A central cone shaped protuberance 8 is integrally molded to the thin membrane 6 and extends outwardly away from the oral condom 2. What is unique about the cone shaped protuberance 8 is that it conforms to the tongue of a user so that the tongue can be moved more flexibly and readily through the thin membrane 6 of the oral condom 2. This provides a natural sensation that the user is not wearing anything at all. The protuberance 8 also provides for free movement of the tongue of a user. The thin membrane 6 also includes two elongated lateral leg portions 16 and 18 which are extended rearwardly toward the ears of the user.

Referring to FIGS. 1, 2 and 4, there are two detachable ear attachments 20 and 22 which can be reusable after oral, vaginal or anal sex. These two detachable ear attachments 20 and 22 are utilized with the oral condom 2, so that the thin membrane 6 can be secured to the face of a user and the amount of tension on the oral condom 2 against the face of the user can be adjusted. Each ear attachment 20 and 22 is substantially identical, and therefore, one will be described in detail. Each ear attachment has a front end 24 with a front portion 26 and a rear end 28 with an ear engagement portion 30. Each front portion 26 has two equally spaced longitudinal slots 32 for engaging with a respective one end of the two elongated lateral leg portions 16 and 18 which are fitted into the two longitudinal slots 32. They can also be wrapped around the front ends 24 and through the slots 32 of the two ear attachments 20, 22 and doubled back to make a tighter fit, as shown in FIG. 2. The tension on the oral condom 2 is adjusted by adjusting where the ends of two elongated lateral leg portions 16 and 18 are attached to the two ear attachments 20 and 22 respectively. The oral condom 2 can be adjusted to any particular user because of its unique attachment means. The two ear attachments 20 and 22 are partially hooked over and behind the ears of the user and held in place, similar to wearing eyeglasses.

The oral condom 2 is adapted to be fixedly retained upon the face of the user, and thereby prevent sexually transmitted diseases when the user engages in oral, vaginal or anal sex. The oral condom 2 is secured to the face of the user by the two ear attachments 20 and 22. Each ear attachment can be conformed to a particular ear of a particular user.

The thin pliable oval-shaped membrane 6 can be made from several materials. By way of example, the thin pliable oval-shaped membrane 6 can be made of latex or polyurethane material, and the ear attachments 20 and 22 can be made of flexible rubber material which can be bent to conform to any particular ear.

Referring to FIG. 6, there is shown a perspective view of an alternative embodiment of the present invention oral condom 102. Since it functions the same as previously described in the preferred embodiment, the parts are numbered correspondingly with 100 added to each reference number. The alternative embodiment of the present invention is similar to the preceding embodiment except that the two ear attachments 120 and 122 are now integrally molded to the thin pliable oval-shaped member 106. The oral condom 102 is a unitary piece, and the description thereof will not be repeated.

Defined in detail, the present invention is an oral condom used by a user in conjunction with oral, vaginal and anal sex for preventing sexually transmitted diseases, comprising: (a) a unitary disposable thin pliable oval-shaped membrane being conformed to the face and the lips of said user such that the thin membrane covers all area of the face extending from approximately beneath the nostrils to below the chin and the jaw, and substantially all of the cheeks of said user; and (b) said thin pliable oval-shaped membrane having a central cone shaped protuberance extending outwardly and conformed to receive the tongue of said user therein such that the tongue can be moved more readily, a portion conformed to the lips of said user such that the lips can move, and two elongated lateral leg portions integrally molded to said thin membrane and extending rearwardly toward the ears of said user and each having an ear engagement end for partially engaging over and behind the ears of said user; (c) whereby said oral condom is adapted to be fixedly retained upon the face of said user and cover the lips and the tongue thereof, and thereby prevent sexually transmitted diseases when said user engages oral, vaginal or anal sex.

Defined broadly, the present invention is a protective mask used by a user for preventing sexually transmitted diseases, comprising: (a) a unitary thin flexible membrane being conformed to the face and the lips of said user, the thin flexible membrane having a cone protuberance extending outwardly and conformed to receive the tongue of said user, and two side leg portions integrally molded to said thin membrane and extending rearwardly toward the ears of said user and each having an ear engagement end for partially engaging the ears of said user; (b) whereby said oral condom is adapted to be fixedly retained upon the face of said user and cover the lips and the tongue thereof, and thereby prevent sexually transmitted diseases when said user engages in oral, vaginal or anal sex.

Of course the present invention is not intended to be restricted to any particular form or arrangement, or any specific embodiment disclosed herein, or any specific use, since the same may be modified in various particulars or relations without departing from the spirit or scope of the claimed invention hereinabove shown and described of which the apparatus shown is intended only for illustration and for disclosure of an operative embodiment and not to show all of the various forms or modifications in which the present invention might be embodied or operated.

The present invention has been described in considerable detail in order to comply with the patent laws by providing full public disclosure of at least one of its forms. However, such detailed description is not intended in any way to limit the broad features or principles of the present invention, or the scope of patent monopoly to be granted.

What is claimed is:

1. An oral condom used by a user in conjunction with oral, vaginal and anal sex for preventing sexually transmitted diseases, comprising:
   a. a unitary disposable thin pliable oval-shaped membrane being conformed to the face and the lips of said user such that the thin membrane covers all area of the face extending from approximately beneath the nostrils to below the chin and the jaw, and substantially all of the cheeks of said user; and
   b. said thin pliable oval-shaped membrane having a central cone shaped protuberance extending outwardly and conformed to receive the tongue of said user therein such that the tongue can be moved more readily, a portion conformed to the lips of said user such that the lips can move, and two identical elongated opposite parallel lateral leg portions integrally molded to said thin membrane and extending rearwardly toward the ears of said user and each having an identical ear engagement end for partially engaging over and behind the ears of said user;
   c. whereby said oral condom is adapted to be fixedly retained upon the face of said user and cover the lips and the tongue thereof, and thereby prevent sexually transmitted diseases when said user engages in oral, vaginal or anal sex.

2. The invention as defined in claim 1 wherein said thin pliable oval-shaped membrane is made of latex.

3. The invention as defined in claim 1 wherein said thin pliable oval-shaped membrane is made of polyurethane.

4. The invention as defined in claim 1 wherein said ear engagement ends of said two elongated lateral leg portions of said oral condom are made of rubber material.

5. A protective mask used by a user for preventing sexually transmitted diseases, comprising:
   a. a unitary thin flexible membrane being conformed to the face and the lips of said user, the thin flexible membrane having a cone protuberance extending outwardly and conformed to receive the tongue of said user, and two identical opposite side leg portions integrally molded to said thin membrane and extending rearwardly toward the ears of said user and each having an identical ear engagement end for partially engaging the ears of said user;
   b. whereby said oral condom is adapted to be fixedly retained upon the face of said user and cover the lips and the tongue thereof, and thereby prevent sexually transmitted diseases when said user engages in oral, vaginal or anal sex.

6. The invention as defined in claim 5 wherein said thin flexible membrane is made of latex.

7. The invention as defined in claim 5 wherein said thin flexible membrane is made of polyurethane.

8. The invention as defined in claim 5 wherein said ear engagement ends of said two side leg portions of said oral condom are made of rubber material.

9. The invention as defined in claim 5 wherein said protective mask is disposable.

* * * * *